United States Patent
Ilvento

[11] Patent Number: 5,843,132
[45] Date of Patent: Dec. 1, 1998

[54] SELF-CONTAINED, SELF-POWERED TEMPORARY INTRAVENOUS PACING CATHETER ASSEMBLY

[76] Inventor: Joseph P. Ilvento, 905 Via Fruteria, Santa Barbara, Calif. 93110

[21] Appl. No.: 726,701

[22] Filed: Oct. 7, 1996

[51] Int. Cl.⁶ ............................................ A61N 1/362
[52] U.S. Cl. .................. 607/10; 607/36; 206/438
[58] Field of Search .................... 607/2, 9, 10, 33, 607/36; 206/363, 438

[56] References Cited

U.S. PATENT DOCUMENTS

| | | | |
|---|---|---|---|
| 3,195,540 | 7/1965 | Weller | 607/36 |
| 3,866,615 | 2/1975 | Hewson | 607/10 |
| 4,013,081 | 3/1977 | Kolenik | 607/36 |
| 4,365,639 | 12/1982 | Goldreyer . | |
| 4,423,732 | 1/1984 | Tarjan et al. | 206/438 |
| 4,444,188 | 4/1984 | Bazell et al. . | |
| 4,444,195 | 4/1984 | Gold | 128/642 |
| 4,723,936 | 2/1988 | Buchbinder et al. | 604/95 |
| 5,044,367 | 9/1991 | Endres et al. | 607/10 |
| 5,109,851 | 5/1992 | Jadvar et al. | 607/10 |
| 5,174,289 | 12/1992 | Cohen | 607/9 |
| 5,397,304 | 3/1995 | Truckai | 604/95 |
| 5,487,757 | 1/1996 | Truckai et al. | 607/122 |
| 5,533,967 | 7/1996 | Imran | 604/95 |
| 5,626,621 | 5/1997 | Koglund et al. | 607/9 |

Primary Examiner—William E. Kamm
Assistant Examiner—George R. Evanisko
Attorney, Agent, or Firm—Lyon & Lyon LLP

[57] ABSTRACT

A self-powered, self-contained, intravenous pacing catheter assembly for use in temporary intravenous cardiac pacing therapy, wherein all components of the assembly may be operated and maintained in a sterile environment proximate a patient entry site. In a preferred embodiment, a miniature pacemaker is powered by an attachable dc battery and outputs a selectable electrical pacing signal over an integrally attached intravenous pacing catheter to an electrode pair located at a distal end of the catheter. The combined pacemaker and catheter assembly are housed inside a sterile see-through pouch having at least one openable panel and an adhesive layer forming a continuous ring around the openable panel upon an exterior surface of the pouch. The pacemaker is preferably manipulable, e.g., by an attending physician, through walls of the sealed pouch, so that a sterile patient seal is not disturbed when changing the output signal settings. For example, in preferred embodiments, the pacemaker unit is cylindrical in shape, with one or more rotatable selector switches disposed about its circumference for ease in manipulating through the walls of the pouch, wherein a "two-hand" locking system is preferably employed to prevent inadvertent movement of settings switches.

18 Claims, 5 Drawing Sheets

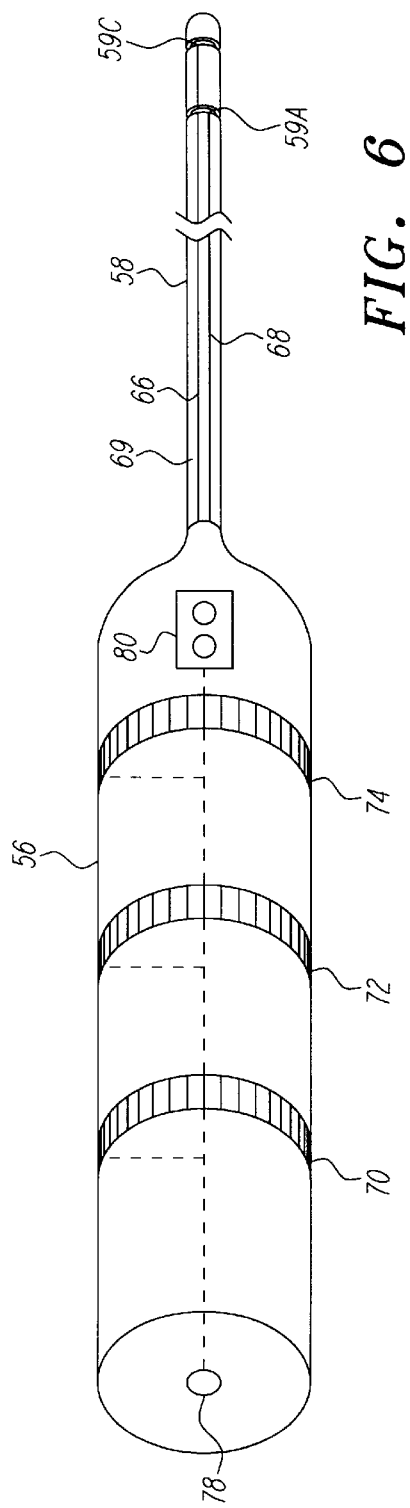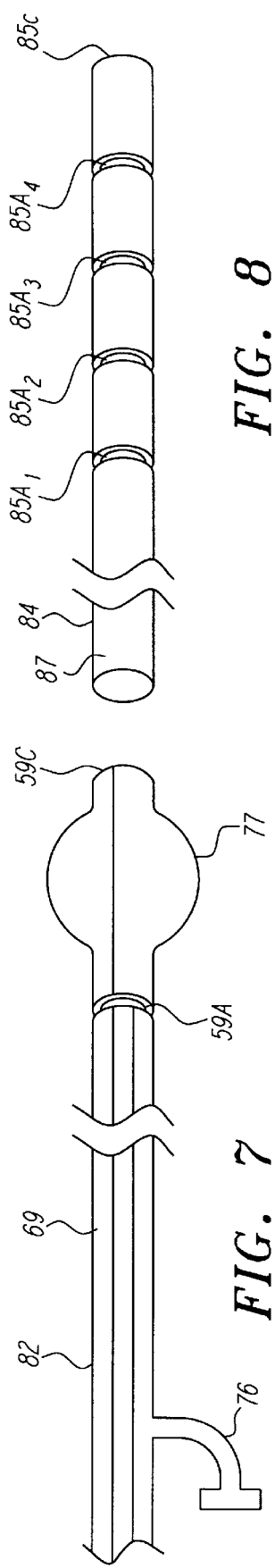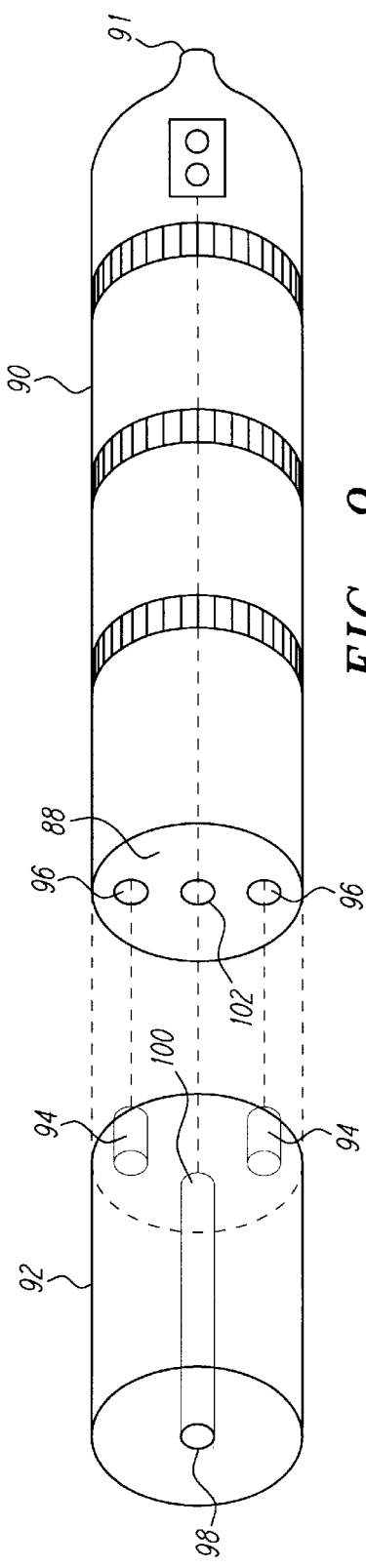

SELF-CONTAINED, SELF-POWERED TEMPORARY INTRAVENOUS PACING CATHETER ASSEMBLY

FIELD OF THE INVENTION

This invention pertains to methods and apparatus for providing temporary intravenous cardiac pacing stimulation.

BACKGROUND

As part of a cardiovascular intervention procedure on a patient, it may be beneficial to provide temporary electrical pacing therapy for stimulating or steadying the heartbeat, or for re-establishing the rhythm of an arrested heart. Often, a temporary cardiac pacing system is used to promote and regulate a rhythmic heart beat without having to implant a permanent internal pacemaker, where the physician is unsure whether a permanent pacemaker is necessary or where the patient is unable to physically endure invasive procedures required for implanting a permanent pacemaker.

An exemplary known external temporary pacing system 20 is depicted in FIG. 1. In particular, the pacing system 20 is used to stimulate the heart of patient 22, shown in a reclining position in a hospital bed 24. A pacemaker unit 26 is suspended from a support stand 28, which may have a fixed or mobile (e.g., casters or wheels) base. The pacemaker 26 generates an electrical pacing signal from an internal dc battery to stimulate the heart of patient 22.

The pacing signal is conducted through patient cable 34 extending from the pacemaker unit 26 to a patient connector 36, which is affixed to the patient (22)'s chest. This creates problems due to the need to manipulate a non-sterile pacemaker unit by the physician, whose hands are sterile. The patient connector 36 relays the pacing signal onto a pacing catheter 42, which is inserted intravenously into the patient (22)'s cardiovascular area through an entry site 40. (The portion of pacing catheter 42 located in the patient's body is shown as a dashed line). At the distal end of pacing catheter 42 are pacing electrodes 44, which output the pacing signal generated by the pacemaker unit 26 to the patient (22)'s ventricle area. Notably, the patient entry site 40 and pacing catheter 42 are isolated from the non-sterile external environment by a protective adhesive bandage 46. A block flow chart depicting the electrical path of the temporary cardiac pacing system 20 is depicted in FIG. 2, wherein the area within the dashed line corresponds to the sterile area (indicated by "S") under bandage 46; and the area outside the dashed line corresponds to the non-sterile external environment (indicated by "NS").

The afore-described system 20 is problematic, however, in that it substantially hinders patient mobility. In particular, the pacemaker unit 26 must stay within the length of the patient cable 34 from the patient connector 36. Thus, moving the patient 22, e.g., to another room or examining area, requires that the pacemaker unit 26, and perhaps stand 28, also be moved. Another problem with system 20 is that a properly positioned pacing catheter 42 is easily displaced by movement of the patient cable 34, e.g., if the cable were tripped over or the patient were to attempt to roll over onto their side. Movement of the pacing catheter 42 can have serious consequences as the catheter may lose capture and be unable to maintain a heart beat.

Another issue that is important for using intravenous devices is the maintenance of a sterile environment around the entry site 40. As can be observed in FIG. 2, the external pacemaker system 20 requires the use of a non-sterile patient cable 34 and connector interface 36. This can be problematic, since maintaining a good electrical connection between the patient connector 36 and pacing catheter 42 requires an unobstructed electrical contact, while maintaining a sterile entry site requires obstructing and isolating the patient connector 36 and pacing catheter 42 as much as possible.

Thus, it is desirable to provide a superior temporary pacing system, which overcomes the afore-described problems of the prior art.

SUMMARY OF THE INVENTION

The present invention provides a self-powered, self-contained, intravenous pacing catheter assembly for use in temporary intravenous cardiac pacing therapy, wherein all components of the assembly may be operated and maintained in a sterile environment proximate a patient entry site. In particular, a battery-powered pacemaker and pacing catheter are provided as a single, completely sterile unit, which allows the physician to manipulate and test the entire system, while maintaining complete patient sterility.

In a preferred embodiment, a miniature pacemaker is powered by an attachable dc battery and outputs a selectable electrical pacing signal over an integrally attached intravenous pacing catheter to an electrode pair located at a distal end of the catheter. The combined pacemaker and catheter assembly are housed inside a sterile see-through pouch having at least one openable panel. In accordance with one aspect of the invention, an adhesive layer is provided upon an exterior surface of the pouch, forming a continuous ring around the openable panel. A cover strip is placed over the adhesive layer prior to use. The pacemaker is preferably manipulable, e.g., by an attending physician, through walls of the sealed pouch, so that a sterile patient seal is not disturbed when changing the output signal settings. For example, in preferred embodiments, the pacemaker unit is cylindrical in shape, with one or more rotatable selector switches disposed about its circumference for ease in manipulating through the walls of the pouch, wherein a "two-hand" locking system is preferably employed to prevent inadvertent movement of settings switches.

To use the pacing assembly, a patient entry site is first prepared and sterilized by an attending physician and the pouch is placed over the site, with the openable panel positioned directly over the entry opening. The cover strip is removed from the adhesive layer and the panel opened, and then the pouch is depressed against the patient's skin, the adhesive layer thereby forming a seal between the skin of the patient and the contents of the pouch. In this manner, a sterile environment is maintained over the entry site. The pacing catheter is then directed by the physician from the pouch into the entry site—i.e., by manual manipulation directly through the walls of the pouch—until the electrode pair reaches the patient's ventricle area. The physician then verifies ventricle capture by manipulating the distal location of the electrodes and, if necessary, manipulating external controls on the pacemaker directly through the walls of the pouch.

In accordance with another aspect of the invention, an auto-capture verification is provided by a microprocessor in the pacemaker, e.g., which can recognize the wave form signature of pacing "capture" of the ventricle. Further aspects include the use in some preferred embodiments of multiple electrodes spaced along a distal end of the pacing catheter, wherein the microprocessor continually evaluates and selects the best pair with which to transmit the pacing signal.

These and other objects, aspects, advantages and features of the present invention will be more fully understood and appreciated by those skilled in the art upon consideration of the following detailed description of a preferred embodiment, presented in conjunction with the accompanying drawings.

BRIEF DESCRIPTION OF THE DRAWINGS

The drawings illustrate both the design and utility of a preferred embodiment of the present invention, in which:

FIG. 6 is a perspective side view of a preferred pacemaker and pacing catheter for use in the catheter assembly of FIG. 3, in accordance with further aspects of the present invention;

FIG. 7 is a perspective side view of an alternate preferred pacing catheter for use in the assembly of FIG. 3, in accordance with still further aspects of the present invention;

FIG. 8 is a perspective side view of yet another alternate preferred pacing catheter for use in the assembly of FIG. 3, in accordance with still further aspects of the present invention; and FIG. 9 is a perspective side view of an alternate preferred pacemaker for use in the catheter assembly of FIG. 3, in accordance with still further aspects of the present invention.

DETAILED DESCRIPTION OF THE PREFERRED EMBODIMENTS

Figure 1:
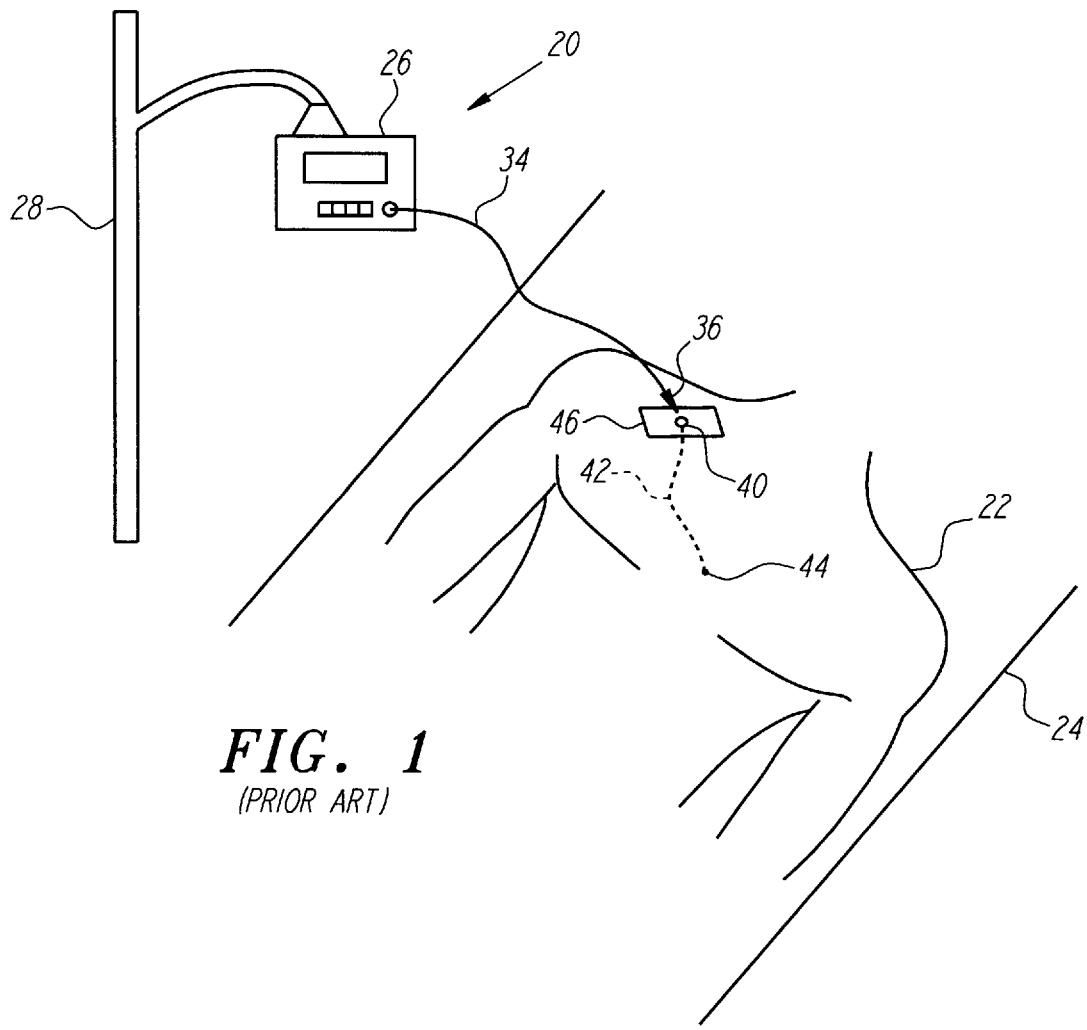
FIG. 1 is a known temporary pacing catheter system.
Figure 2:
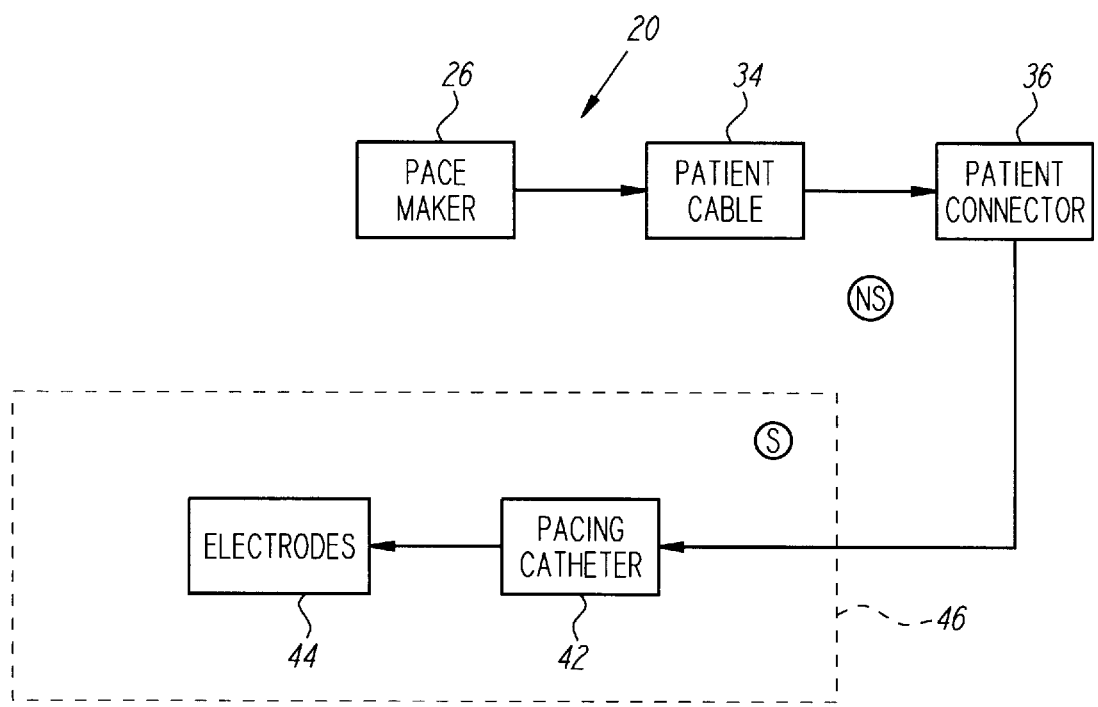
FIG. 2 is a block diagram of the temporary pacing catheter system of FIG. 1.
Figure 3:
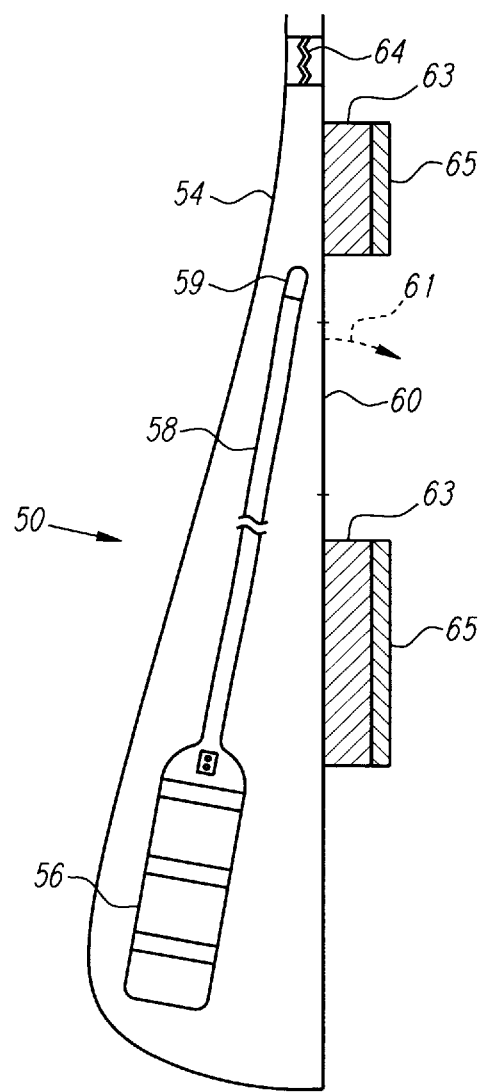
FIG. 3 is a partially cut-away side view of a preferred self-contained, self-powered temporary intravenous pacing catheter assembly, in accordance with aspects of the present invention.

Referring to FIG. 3, a temporary intravenous pacing catheter assembly 50 includes a battery-powered pacemaker 56 integrally attached to a pacing catheter 58, both of which are housed inside a sealable, see-through, sterile pouch 54. In accordance with a first aspect of the present invention, the pacemaker 56 is manipulable, e.g., by an attending physician, through walls of the sealed pouch 54, so that the sterile environment within the pouch 54 is not disturbed when changing output signal settings.

Figure 4:
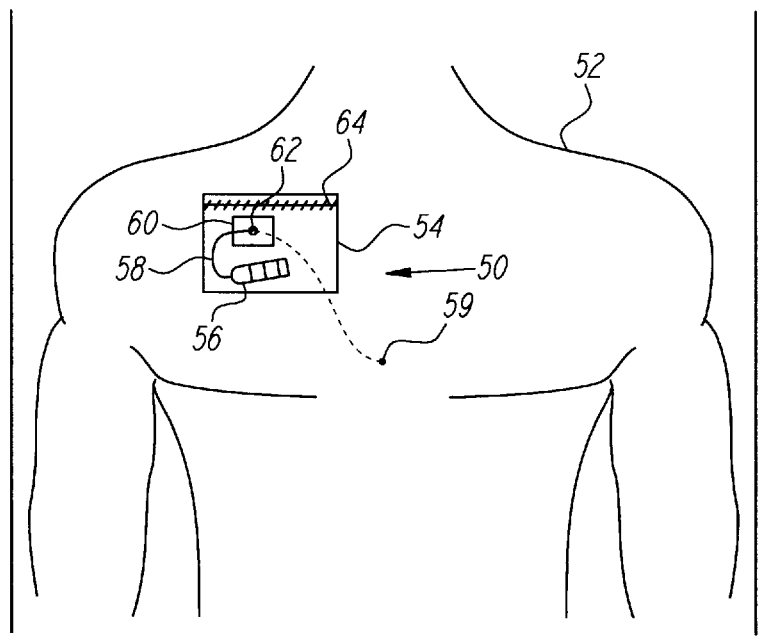
FIG. 4 is a top perspective view of the catheter assembly of FIG. 3, in use with a patient.

FIG. 4 shows the catheter assembly 50 in use with a patient 52. Referring to both FIGS. 3 and 4, prior to inserting the pacing catheter 58, a patient entry site 62 is first prepared and sterilized by an attending physician. The pouch 54 is then placed over the site 62, wherein an openable, or removable panel 60 located in a wall of the pouch 54 positioned directly over the entry site 62. An adhesive layer 63 surrounds the openable panel 60 on the respective exterior surface of the pouch 54 contacting the patient 52, forming a continuous ring around the open panel 60. A cover strip 65 is removed from the adhesive layer 63, the panel 60 opened (as indicated by the arrow 61 in FIG. 3), and the pouch 54 depressed against the patient 52's skin. In this manner, the adhesive layer 63 forms a seal between the patient 52's skin and the contents of the pouch 54, wherein a sterile environment is maintained over the entry site 62.

The pacing catheter 58 is then directed by the physician from the pouch into the entry site 62 by manual manipulation directly through the walls of the pouch 54, until a distally located electrode pair 59 reaches the patient 52's ventricle area. The pacemaker 56 generates an electrical pacing signal, which is transmitted via wires in the pacing catheter 58 to the electrodes 59. An attending physician preferably verifies ventricle capture by the pacing signal, moving the catheter until the electrodes 59 are correctly positioned—, i.e., generally in the right chamber or ventricle of the patient's heart. It may also be necessary for the physician to manipulate external controls on the pacemaker 56 through the walls of the pouch 54, until capture is obtained. Capture is verified by a conventional, externally generated electrocardiograph signal.

In preferred embodiments, the pouch 54 is made from a material that allows a doctor to easily manipulate and adjust the external controls on the pacemaker 56, without opening pouch 54—, i.e., a material that is both reasonably light and substantially transparent. An example of a suitable material includes the commericially available clear plastic material used in "Op-site" wound covers. The openable panel 60 may configured to be secured back over the entry site 62 once the pacing catheter 58 is properly positioned, in order to help secure the catheter 58 in place. If necessary, the pouch 54 may be opened through a openable seal 64.

Figure 5:
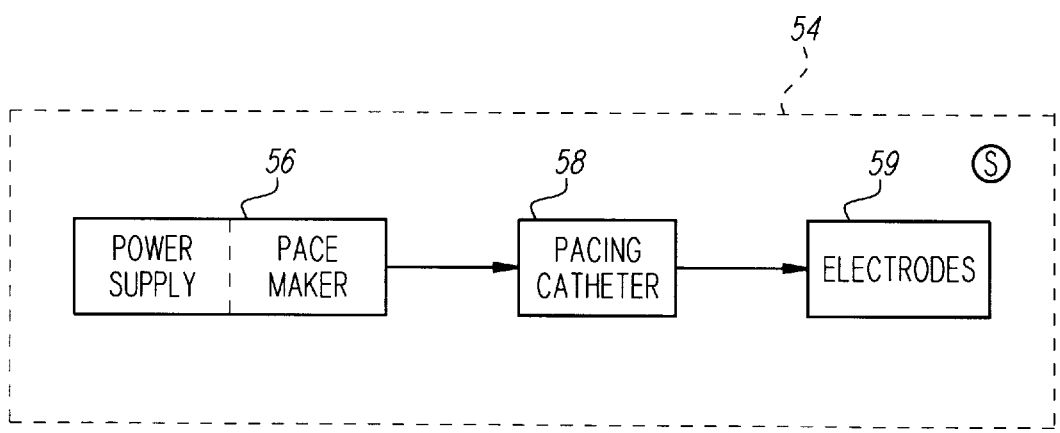
FIG. 5 is a block diagram of the catheter assembly of FIG. 3.

A block flow chart depicting the preferred temporary cardiac pacing system 50 is depicted in FIG. 5, wherein the area within the dashed line corresponds to the sterile area (indicated by "S") maintained within the see-through pouch 54 and patient entry site 62.

Referring to FIG. 6, the pacemaker 56 is generally cylindrical in shape and has three rotatable control dials 70, 72 and 74, which may be rotated with respect to its external circumference. The control dials 70, 72 and 74 are used to manipulate the output settings of pacemaker 56. For example, dial 70 can be used to adjust the signal transmission rate of the pacing signal; dial 72 can be used to adjust the amplitude (i.e., voltage potential) of the pacing output signal; and dial 70 can be used to alter the sensitivity to feedback received from the heart. A locking button 78 must be depressed in order to allow manipulation (i.e., rotation) of the dials 70, 72 and 74, which are otherwise "locked" in place to prevent patient movements or other jarring from changing the settings of pacemaker 56. The pacemaker 56 includes an internal dc battery (not shown in FIG. 6), that provides a dc input voltage to the pacemaker 56, preferably with a capacity for lasting at least six, but more optimally ten days. The battery should also have a shelf life of approximately two to three years.

The pacing catheter 58 contains a lumen 69 in its interior and includes near its distal end an anode electrode 59A and a cathode electrode 59C. Both the anode 59a and cathode 59C receive a voltage signal via a pair of wires 66 and 68, respectively, from internal signal generation circuitry (not shown), the potential difference between the respective anode 59A and cathode 59C representing the pacing signal used to stimulate the heart. Pin connectors 80 reside on the pacemaker 56 and provide for the connection of an external pacemaker unit (not shown), to the pacing catheter 58 and electrodes 59A and 59C, respectively, in case the pacemaker 56 fails, without having to disturb the pacing catheter 58.

The pacemaker 56 preferably also includes a microprocessor (not shown) that allows direct control of the output pacing signal wave form. This can be accomplished, by way of example, by including a pressure transducer (not shown) at the distal end of pacing catheter 58, which can determine the blood flow pressure and from this signal a microprocessor can adjust the magnitude and timing of the pacing signal. Further, the use of a microprocessor allows the determination of capture verification, since the microprocessor can calculate the magnitude and timing of a heart beat as supplied from the pressure transducer. The microprocessor is preferably programmable and can perform various function such as impedance calculations of the myocardial tissue between the respective anode and cathode electrodes 59A and 59C.

Referring to FIG. 7, an alternate preferred pacing catheter 82 includes an luer type connector 76 proximate the distal end (i.e., where the pacing catheter 82 is connected to the pacemaker 56) to allow for insertion of an air syringe that is used to introduce air into the internal lumen 69, in order to inflate a balloon 77 located at the distal end of pacing catheter 82 (i.e., between anode 59A and cathode 59C). In particular, the balloon 77 can be inflated once pacing catheter 82 is inserted into the entry, so that the blood flow inside the blood vessel will carry the distal end of the pacing catheter 82 into the right ventricle of the heart. Once in the right ventricle, balloon 88 is deflated, so that the position of pacing catheter 82 is more easily maintained.

Referring to FIG. 8, yet another alternate preferred pacing catheter 84 has multiple anode electrodes 85A$_{1-4}$ located along a distal end to allow for ease in ventricle capture by the pacing signal. In particular, the multiple anode electrode arrangement 85A$_{1-4}$, along with a pacemaker microprocessor (not shown), allows for automatic capture by switching between the various anode electrodes 85A$_{1-4}$ paired with the cathode 85C, until a capture is verified. For instance, the microprocessor can measure the magnitude of a heart beat produced by each respective anode 85A$_{1-4}$ paired with the cathode 85C, versus the most prior signal produced by the same set of pacing electrodes. If the later heart beat is not of a required level or less then most prior signal, the microprocessor can cause the pacemaker 56 to output its pacing signal via the next anode 85A$_{1-4}$, until a match is verified. By repeating the process, the microprocessor can find the optimal combination of electrodes for stimulating the patient's heart. In this instance, respective anode connection wires (not shown) are provided in a lumen 87 of the pacing catheter 84 for each of the anode electrodes 85$_{1-4}$. As will be apparent to one skilled in the art, alternate preferred embodiments may be provided with multiple cathode electrodes, which may be selectively paired with a single anode electrode in the same manner, until a capture is verified.

Referring to FIG. 9, an alternate preferred pacemaker 90 is configured to have a removable battery pack 92 fitted onto its end 88 distal the pacing catheter connection 91. In this configuration, releasable snap-on leads 94 extending from the battery pack 92 connect with retaining leads 96 on end 88 of the pacemaker 90, to both secure the battery pack 92 to the pacemaker 90, as well as to provide an electrical connection to supply dc voltage. The battery pack 92 may be the main battery for the pacemaker 90, or may be an add-on unit, if the main battery fails or runs low. The battery pack 92 is provided with an extension assembly button 98 and plunger 100, to depress an unlocking button 102 for the controls of the pacemaker 90.

Thus, an innovative self-powered and self-contained intravenous pacing catheter assembly has been disclosed and described. While the foregoing detailed description was directed to a temporary self-contained, self-powered pacing catheter, it will be apparent to those skilled in the art that the described pacing catheter methodology and architecture can be effectively practiced with any catheter assembly utilizing electrical signals. For example, while the present invention is particularly well suited for pacing, it may be equally employed for use in defibrillation or other electrical-based cardiovascular therapies.

As would be apparent to those skilled in the art, many more modifications are possible without departing from the inventive concepts herein. The inventions, therefore, are not to be restricted except in the spirit of the appended claims.

What is claimed is:

1. A temporary pacing assembly, comprising:
   an external pacemaker having an integral power supply and manually adjustable controls for outputting and adjusting a pacing signal for providing cardiac stimulation; and
   a transvenous pacing catheter including an electrode pair disposed at a distal end to supply the pacing signal to a patient's heart,
   wherein the pacemaker and pacing catheter are provided in a sealable sterile container having a removable wall portion.

2. The pacing assembly of claim 1, wherein the pacemaker is cylindrical shaped and has a circumferentially disposed rotatable control dial.

3. The pacing assembly of claim 2, wherein the pacemaker further comprises a locking mechanism, which selectively prevents the control dial from being rotated.

4. The pacing assembly of claim 1, wherein the container further comprises an adhesive layer substantially surrounding the removable wall portion.

5. The pacing assembly of claim 1, wherein the pacemaker is cylindrical shaped and has a circumferentially disposed rotatable control dial, and wherein the container is made of a sufficiently flexible and thin material to allow for manual manipulation of the pacing catheter and of the control dial.

6. The pacing assembly of claim 1, wherein the pacing catheter comprises at least three electrodes, which may be selectively paired in order to supply the pacing output signal to a patient's heart.

7. The pacing assembly of claim 1, wherein the pacemaker is configured to have an external battery pack attached thereto.

8. The pacing assembly of claim 1, wherein the pacemaker further comprises a pin connector configured to receive an external pacing signal and deliver the externally received pacing signal to the pacing catheter.

9. The pacing assembly of claim 1, wherein the pacemaker is cylindrical shaped and has a circumferentially disposed rotatable control dial, and wherein the pacemaker further comprises a pin connector configured to receive an external pacing signal and deliver the externally received pacing signal to the pacing catheter.

10. A temporary external pacing assembly, comprising:
    a pacemaker having an integral power supply and outputting a pacing signal for providing cardiac stimulation;
    a pacing catheter integrally attached to the pacemaker, the pacing catheter including an electrode pair disposed at a distal end to supply the pacing signal to a patient's heart; and
    a sealable, sterile container having a removable wall portion, wherein the pacemaker and pacing catheter are sterile and are stored in the container.

11. The pacing assembly of claim 10, wherein the pacemaker is cylindrical shaped and has a circumferentially disposed rotatable control dial, wherein the container is made of a sufficiently flexible and thin material to allow for manual manipulation of the pacing catheter and of the control dial, and wherein the container has an adhesive layer substantially surrounding the removable wall portion.

12. The pacing assembly of claim 10, wherein the pacemaker is cylindrical shaped and has a circumferentially disposed rotatable control dial.

13. The pacing assembly of claim 12, wherein the pacemaker further comprises a locking mechanism, which selectively prevents the control dial from being rotated.

14. The pacing assembly of claim 13, wherein the pacemaker is configured to have an external battery pack connected thereto.

15. The pacing assembly of claim 10, wherein the pacing catheter comprises at least three electrodes, which may be selectively paired in order to supply the pacing signal to a patient's heart.

16. A temporary external pacing assembly, comprising:
   a cylindrical shaped pacemaker having a circumferentially disposed rotatable control dial, the pacemaker further comprising a locking mechanism that selectively prevents the control dial from being rotated; and
   a pacing catheter integrally attached to the pacemaker, wherein the pacemaker and pacing catheter are sterile and are stored in a sealable, sterile container made of a sufficiently flexible and thin material to allow for manual manipulation therethrough of the pacing catheter and of the control dial, the container further comprising a removable wall portion and an adhesive layer, the adhesive layer substantially surrounding the removable wall portion.

17. The pacing assembly of claim 16, wherein the pacemaker is configured to have an external battery pack connected thereto in a manner that, when the battery pack is attached, still allows for operation of the locking mechanism.

18. The pacing assembly of claim 16, wherein the pacing catheter comprises at least three electrodes, which may be selectively paired in order to supply a pacing signal to a patient's heart.

* * * * *